United States Patent [19]
Quackenbush

[11] Patent Number: 5,104,705
[45] Date of Patent: Apr. 14, 1992

[54] EXTRUDED POLYMER TUBES FOR BLOOD AND FLUID SAMPLING

[75] Inventor: John J. Quackenbush, Hoover, Ala.

[73] Assignee: FBK International Corporation, Birmingham, Ala.

[21] Appl. No.: 284,589

[22] Filed: Dec. 15, 1988

[51] Int. Cl.⁵ .................................................. A61B 5/14
[52] U.S. Cl. .................. 428/36.91; 128/763; 428/141
[58] Field of Search ............... 128/763, 768; 428/36.9, 428/36.91, 141; 422/100

[56] References Cited

U.S. PATENT DOCUMENTS

| | | | |
|---|---|---|---|
| 4,210,156 | 7/1980 | Bennett | 128/763 |
| 4,301,414 | 11/1981 | Hill et al. | 29/876 |
| 4,305,983 | 12/1981 | Hoppe et al. | 428/36.9 |
| 4,389,366 | 6/1983 | Hoesslin et al. | 264/565 |
| 4,589,421 | 5/1986 | Ullman | 128/763 |
| 4,791,938 | 12/1988 | Van Valkenburg | 128/763 |

Primary Examiner—James Seidleck
Attorney, Agent, or Firm—Stanger, Michaelson, Spivak & Wallace

[57] ABSTRACT

Plastic replacements for glass capillary tubes for drawing samples of blood or other body fluids are achieved by texturing the inside surface of the tube with uniform fine features and by extruding the tube over a suitably textured tapered pin with a (gradual) ratio of at least 6:1 during extrusion to ensure the transfer of the pin's surface texture to the inside diameter of the tube.

4 Claims, 2 Drawing Sheets

EXTRUDED POLYMER TUBES FOR BLOOD AND FLUID SAMPLING

FIELD OF THE INVENTION

This invention relates to a plastic capillary tube replacement for glass capillary tubes in common use for taking blood samples.

BACKGROUND OF THE INVENTION

Small diameter glass capillary tubes are commonly used in medicine to draw blood or other fluid samples from a small puncture wound made in a patient's finger or other anatomically necessary site. These glass tubes typically have an inside diameter on the order of 0.021" and an outside diameter on the order of 0.060". Typically, the wall thickness of such a tube is about 0.0195" with a cut length of 3.000". Although tubes of different sizes can be used depending on blood type and type of test performed, all the tubes are very small-diameter tubes which draw blood by virtue of the inherent capillary action of the tube.

Glass tubes operative by virtue of the inherent capillary action of the small bore are called "hematocrits" and are used in conjunction with charts which show visually post-test results by holding the column of blood against the chart thus providing a simple, quick and highly accepted test procedure to determine plasma level as is well known.

Although hematocrits have been used for many years not only to take blood samples but also to perform post-test and sample blood analysis, there are a number of disadvantages to the use of glass tubes. One disadvantage is that the tubes are not disposable readily and cannot be incinerated in conventional hospital or other common institutional incinerators. Thus, once used and possibly contaminated with blood which may carry hepatitis or other viruses such as those identified with AIDS, these tubes are taken to local landfills where they can pose a continuing health hazard.

Another disadvantage to the use of glass hematocrits is that they are fragile and may be broken, cracked, or chipped easily. Consequently, it is possible for the user to come into intimate contact with virus-contaminated blood and possibly become infected. Even though latex gloves may be used when taking blood samples, an obvious hazard is that a chipped tube could puncture the glove inadvertently and break through the skin of the user.

Hematocrits are also difficult to produce to close tolerances. Glass is inherently fragile, silica-based and subject to wide fluctuations in temperature during processing. These factors create variations in the inner and outer dimensions of such small diameter tubes. Such variations compound errors in blood sample tests which must be measured precisely.

BRIEF DESCRIPTION OF AN EMBODIMENT OF THIS INVENTION

The present invention is directed at a plastic Hematocrit-replacement tube which is unbreakable, precision dimensioned, can be made in a variety of sizes, will not chip or break, is water clear, has no sharp edges, can be heparinized if required and which exhibit excellent capillary action. Test results on plastic tubes designed to replace glass Hematocrits have been found to exhibit unpredictable capillary action at best. Only when the tubes were extruded employing an inner tapered sizing pin of "gradual" dimensions of at least 6 to 1 and only when that pin surface was textured with super-fine sand or talc could predictable capillary action be obtained. The textured pin surface produced a consistently smooth interior surface on the extruded tubing which eliminated flow lines and provided a suitable "wet out" surface for achieving the requisite capillary action. Blood sampling tubes made from Polyurethane polymer hold close-tolerance dimensions of ±0.0015" or less, can be cut precisely by conventional, in-line tube cutting equipment capable of maintaining necessary cut length accuracy and have been found in test procedures to draw 1.5 microliters of blood in 3 seconds, a performance equal to commonly used Hematocrits.

In another embodiment, a Hematocrit replacement was made with inner and outer layers of different materials. The inner layer comprised Dow chemicals' Pellethane 2363-75DE and the outer layer was Goodyear's P.E.T plastic G-7207. The latter material is harder than polyurethane and increases the rigidity of the extruded tube. The composite material is extruded with a die having an extrusion pin with the land length and surface texture described above. Predictable capillary action is exhibited.

DETAILED DESCRIPTION

Figure 1:
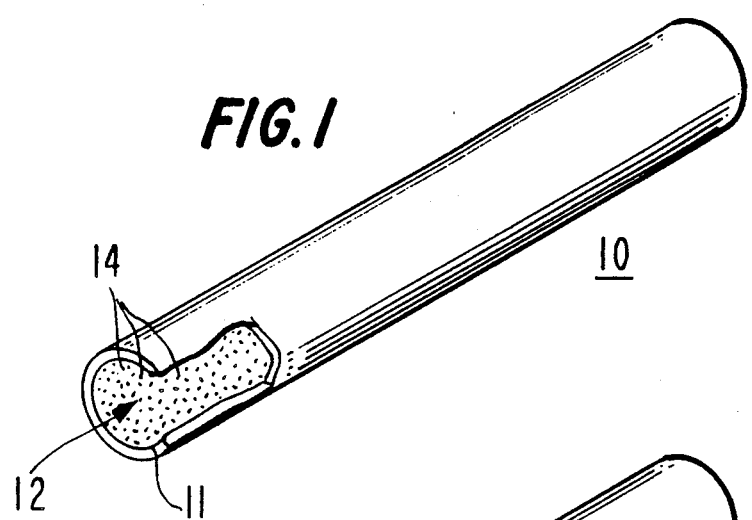
FIGS. 1 and 2 are schematic representation of a plastic hematocrit-replacement tube, partially broken away made in accordance with the invention.

FIG. 1 shows a plastic hematocrit-replacement tube 10 in accordance with one aspect of this invention. The tube is three inches long to correspond to the standard length of glass hematocrits in common use. The tube has a single layer 11 with a thickness of 0.0195 inch with inside and outside diameters of 0.021 inch and 0.060 inch respectively.

The tube is shown partially broken away to expose the interior surface 12 of the layer. Surface 12 is formed in a manner to exhibit a reduced surface tension so that the tube is operative to draw blood by capillary action. A surface with suitably reduced surface tension exhibits a uniform feature size of from about one micron to about seventy five microns represented by dots 14.

Figure 2:
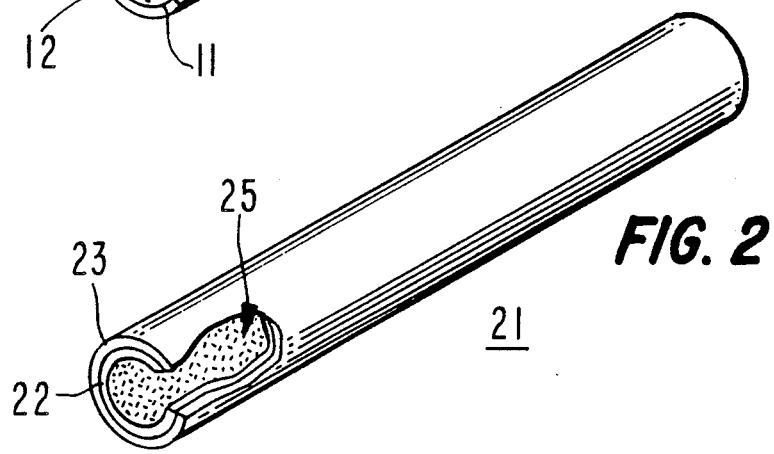

FIG. 2 shows a second hematocrit-replacement tube 21 in accordance with another aspect of this invention. Tube 21 comprises inner and outer layers 22 and 23 respectively. Once again, the tube is three inches long and the inside diameter of the tube is 0.021 inch and 0.0195 inch thick. But the outside layer is six to eight times thicker than the inner layer. Also, inner surface 25 of layer 22 also is formed with a uniform feature size of from about one micron to about seventy five microns in order to achieve the desired reduced surface tension and thus the desired capillary action.

A variety of materials may be used for the tubes of FIGS. 1 or 2. The material of FIG. 1 or for the inner layer of the tube of FIG. 2 ideally comprise a class VI, medical grade extrudable polymer which meets the FDA class VI toxicity test. Such materials are either based, wettable and water clear. The outer layer of the tube of FIG. 2 is used to impart rigidity to the tube and ideally comprises a polyethelene tetraflouride (P.E.T), class VI approved material also. Various illustrative materials suitable for mono or coextruded plastic hematocrit-replacement tubing which can be made to exhibit predictable and suitable capillary action as listed in the following table along with their suppliers.

| Material | Supplier |
| --- | --- |
| Polypropylene | Eastman Temite, Himont |
| Polyurethane | Goodyear, Estane |
| Nylon | Allied, DuPont |
| P.E.T | Goodyear |
| EVA copolymers | U.S.I., DuPont, Dow |
| Acrylics | Allied, DuPont |

Figure 3:
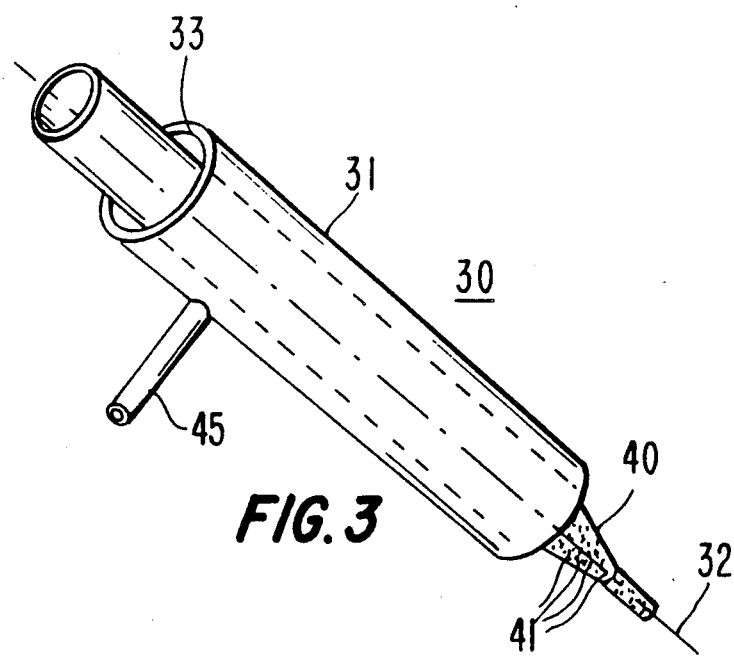
FIG. 3 is a schematic representation of a portion of an extrusion die for making the hematocrit-replacements of FIGS. 1 and 2.

The tubes of FIGS. 1 or 2 are made by extrusion through an extrusion die. FIG. 3 shows such a die 30 schematically. Die 30 comprises an outer cylindrical casing 31 with a cylindrical mandrel within the casing. Both the casing and the mandrel are fixed in position along central axis 32, in a manner to define a thin opening (sizing ring) 33 between them. The mandrel terminates in an inner tapered sizing pin which controls the inside diameter of the extruded tubing.

Figure 4:
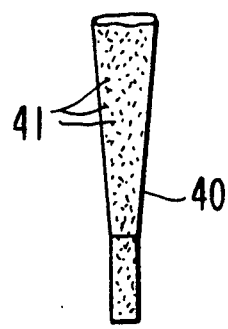
FIG. 4 is a schematic representation of a pin portion of the die of FIG. 3.

FIG. 4 shows the tapered sizing pin 40 also schematically. Pin 40 has a textured surface formed by exposure to super-fine sand or talc under pressure to "blast" the surface of the pin. The texturing is represented by dots 41 in both FIGS. 3 and 4. The sand or talc is blown at the surface of the pin via a hose in a well understood manner.

In order to emboss the interior wall of the tubes of FIGS. 1 or 2, the land length of the pin is such that the ratio of the pin length to the maximum diameter of the pin is six to one or more and with relatively hard materials such as DOW 2365-75DE materials is as much as twelve to one. The reason for such a land length is to permit sufficient contact between the pin and the inside wall of the tube during the extrusion process to ensure uniform embossing of the interior wall so that the requisite capillary action is produced.

The embossing process and the need for an adequate gradual land length can be appreciated by a consideration of FIGS. 3 and 4. The compliant raw material is introduced into the sizing ring 33 under pressure, in a manner well understood. The material cools as it advances into a tube before it contacts the surface of pin 40; but the interior of the surface is still compliant to permit embossing by the surface texture of the pin.

If an outer layer is used to make a tube of the type shown in FIG. 2, the material of the outer layer is introduced downsteam from the point at which the material of the inner tube is introduced. A part for the introduction of the material of the outer layer is shown as 45. The die configuration and the manner of introduction of materials to such a die form coextruded tubes of the type shown in FIG. 2 are well described in connection with FIG. 5.

Figure 5:
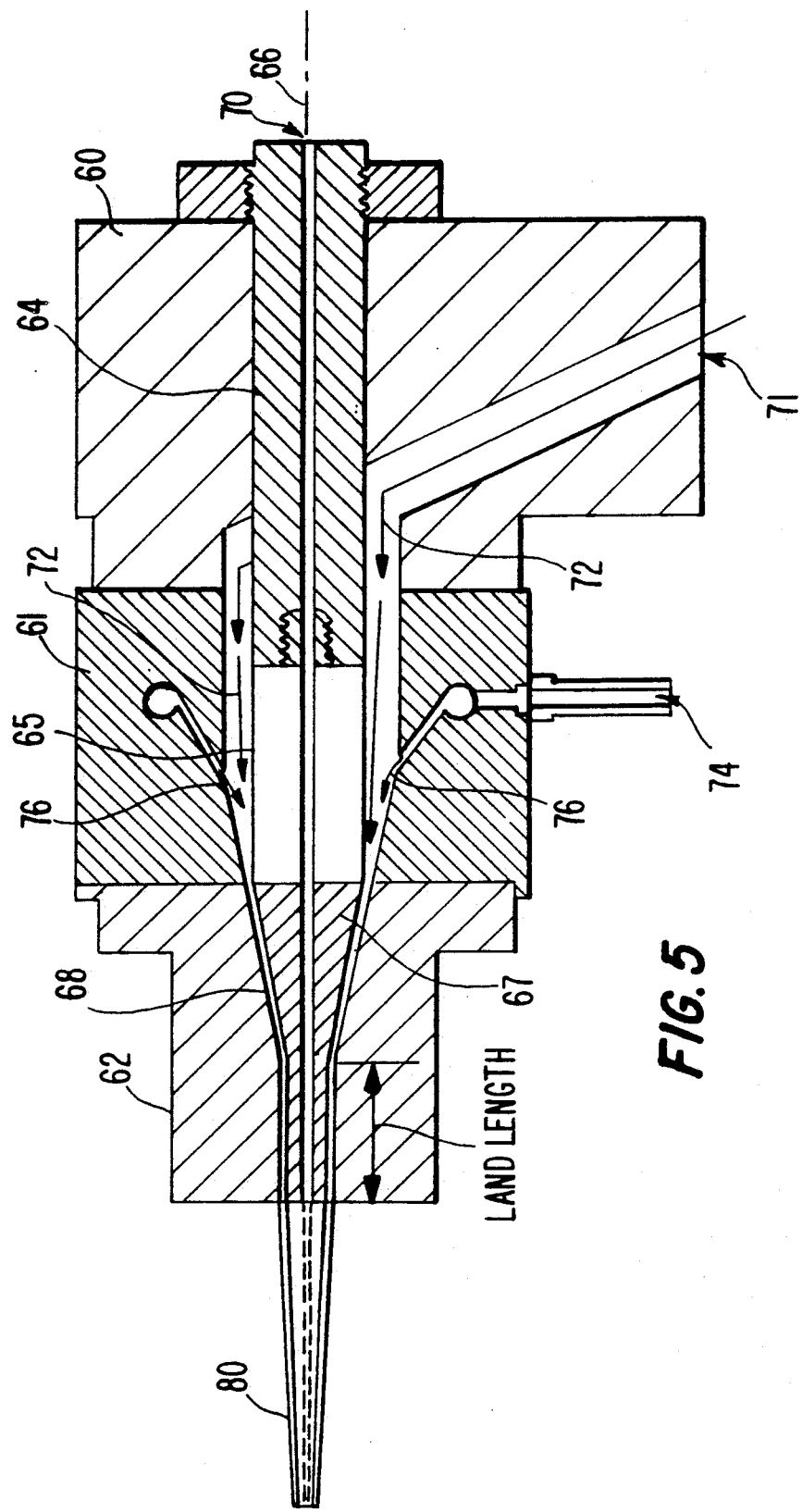
FIG. 5 is a cross sectional view of a dual layer Extrusion die.

The die of FIG. 5 comprises a primary die body 60, a secondary die section "and an outside diameter forming plate 62. A mandrel 64, with a mirror-finish section 65 is fixed within the die along axis 66. A tapered forming pin 67 is positioned to follow "mirror" section 65 in a manner to define a sizing ring 68 with said forming plate.

In operation, air is introduced at 70 along axis 66 to the right as viewed in the figure. The material for the inner layer is introduced at 71 and follows the direction of arrows 72. This material may be, for example, polyurethane. The material for the outer layer is introduced at 74 and follows the arrows 72. Such a material may comprise PET for example.

During tube formation, the double-layered tube moves into the sizing ring along tapered forming pin 67 in a manner to texture the inside surface of the tube. The land length portion of the tapered forming pin is labelled for convenience.

The extruded double-layer tube is drawn down to the desired size by tapered extension 80.

Extrusion equipment employing dies and tapered pins of the type shown in FIGS. 3 and 4 is adopted to extrude tubing of the type shown in FIGS. 1 or 2 continuously. It is clear that such tubing can be cut into three inch segments by conventional, in-line cutting equipment to provide replacements for glass hematocrits.

What is claimed is:

1. A plastic tube adapted to draw fluids via capillary action, said tube including an inner surface having a finely textured surface, said diameter and texture being of dimensions to draw fluids into said tube by capillary action, said tube having an inside diameter of about 0.021" and an outside diameter of about 0.060", a wall thickness of about 0.0195", said inner surface having a uniform surface texture with a feature size of from about one micron to about seventy five microns, wherein said tube comprises a first inner layer of relatively flexible, extendable plastic capable of exhibiting a textured surface, said inner layer including thereabout an additional layer of relatively rigid extendable plastic.

2. A plastic tube in accordance with claim 1 wherein said first inner layer comprises a polyurethane polymer and said additional layer comprises a P.E.T. plastic.

3. A plastic tube in accordance with claim 1 essentially 3.000" long.

4. A plastic tube in accordance with claim 1 wherein said additional layer is between about 6 to 8 times as thick as said inner layer.

* * * * *